US011845969B2

(12) United States Patent
Park et al.

(10) Patent No.: US 11,845,969 B2
(45) Date of Patent: Dec. 19, 2023

(54) PROCESS OF CONVERTING CARBON DIOXIDE USING COMBINATION OF CARBON DIOXIDE MINERALIZATION PROCESS AND METABOLISM OF SULFUR-OXIDIZING MICROORGANISMS

(71) Applicant: SK Innovation Co., Ltd., Seoul (KR)

(72) Inventors: Woo Chan Park, Daejeon (KR); Kwang Kuk Cho, Daejeon (KR); Taewan Kim, Daejeon (KR); Yeon Hwa La, Daejeon (KR); Jayoung Ryu, Daejeon (KR); Sang Min Lee, Daejeon (KR)

(73) Assignee: SK Innovation Co., Ltd., Seoul (KR)

( * ) Notice: Subject to any disclaimer, the term of this patent is extended or adjusted under 35 U.S.C. 154(b) by 254 days.

(21) Appl. No.: 16/335,852

(22) PCT Filed: Sep. 26, 2017

(86) PCT No.: PCT/KR2017/010616
§ 371 (c)(1),
(2) Date: Mar. 22, 2019

(87) PCT Pub. No.: WO2018/056787
PCT Pub. Date: Mar. 29, 2018

(65) Prior Publication Data
US 2019/0256882 A1  Aug. 22, 2019

(30) Foreign Application Priority Data

Sep. 26, 2016 (KR) .......... 10-2016-0123182
Sep. 26, 2017 (KR) .......... 10-2017-0124179

(51) Int. Cl.
C12P 19/40   (2006.01)
(52) U.S. Cl.
CPC .................. C12P 19/40 (2013.01)
(58) Field of Classification Search
CPC .... C12P 7/02; C12P 7/64; C12P 19/40; C12P 3/00; C12P 1/00; C01B 17/69; C12Y 402/01001
See application file for complete search history.

(56) References Cited

U.S. PATENT DOCUMENTS

2010/0120104 A1* 5/2010 Reed ............... C12P 7/649
435/140
2013/0189750 A1  7/2013  Jin et al.
2014/0335548 A1* 11/2014 Parada Valdecantos ...........
G01N 33/56911
435/7.92
2014/0377814 A1  12/2014  Lee et al.
2016/0082387 A1*  3/2016 Constantz ............ B01D 53/62
423/220

FOREIGN PATENT DOCUMENTS

| CN | 104169427 A | 11/2014 |
|---|---|---|
| KR | 1020100083599 A | 7/2010 |
| KR | 101113803 B1 | 3/2012 |
| KR | 1020130091235 A | 8/2013 |
| KR | 101351464 B1 | 1/2014 |
| KR | 1020150021175 A | 3/2015 |
| KR | 1020150106725 A | 9/2015 |
| KR | 1020150133497 A | 11/2015 |
| KR | 1020160056420 A | 5/2016 |

OTHER PUBLICATIONS

Johnson , Extremophiles: Acidic Environments, Encyclopedia of Microbiology, 3rd edition, p. 107-126 (Year: 2009).*
Pathak et al., Feasibility of Bioleaching in Removing Metals (Al, Ni, V and Mo) from as Received Raw Petroleum Spent Refinery Catalyst: A Comparative Study on Leaching Yields, Risk Assessment Code and Reduced Partition Index, Materials Transactions, vol. 56, p. 1278-1286 (Year: 2015).*
Kim et al., Biomineralization-based conversion of carbon dioxide to calcium carbonate using recombinant carbonic anhydrase, Chemosphere, vol. 87, p. 1091-1096. (Year: 2012).*
Aishvarya et al., "Enhanced inorganic carbon uptake by *Chlorella* sp. IMMTCC-2 under autotrophic conditions for lipid production and CO2 sequestration", Journal of Applied Phycology, 2012, pp. 1455-1463, vol. 24, No. 6.
Romanov et al., "Mineralization of Carbon Dioxide: A Literature Review", ChemBioEng Rev, 2015, pp. 231-256, vol. 2:4.

* cited by examiner

*Primary Examiner* — Taeyoon Kim
*Assistant Examiner* — Tiffany M Gough
(74) *Attorney, Agent, or Firm* — THE WEBB LAW FIRM (57) ABSTRACT

The present invention relates to a process of converting carbon dioxide using a combination of a carbon dioxide mineralization and the metabolism of sulfur-oxidizing microorganisms. According to the process, a carbonate produced in the carbon dioxide mineralization reaction can be converted to a useful substance without supplying an external additional energy source (light, electrical energy, etc.) and mineral resources (metal ions). In addition, the process can be continuously performed by recycling metal ions necessary for the carbon dioxide mineralization reaction.

7 Claims, 5 Drawing Sheets

PROCESS OF CONVERTING CARBON DIOXIDE USING COMBINATION OF CARBON DIOXIDE MINERALIZATION PROCESS AND METABOLISM OF SULFUR-OXIDIZING MICROORGANISMS

CROSS-REFERENCE TO RELATED APPLICATIONS

This application is the United States national phase of International Application No. PCT/KR2017/010616 filed Sep. 26, 2017, and claims priority to Korean Patent Application Nos. 10-2016-0123182 and 10-2017-0124179, filed Sep. 26, 2016 and Sep. 26, 2017, respectively, the disclosures of which are hereby incorporated by reference in their entirety.

TECHNICAL FIELD

The present invention relates to a process of converting carbon dioxide to a useful substance, and more particularly to a process capable of continuously converting carbon dioxide to a useful substance using a combination of a carbon dioxide mineralization process and the metabolism of sulfur-oxidizing microorganisms.

BACKGROUND ART

Combustion of fossil fuels such as coal, oil and natural gas for energy production is a major cause of the increase in concentration of atmospheric carbon dioxide, which contributes to global warming. 0.95 kg of carbon dioxide is emitted to produce 1 kWh of electricity. To reduce these carbon dioxide emissions, various technologies have been developed, such as geological carbon dioxide capture, storage and conversion. In particular, a carbon dioxide mineralization process is a representative carbon sequestration method that reduces carbon dioxide by long-term sequestration of atmospheric carbon dioxide. Accordingly, a technique which mineralizes carbon dioxide into a metal carbonate compound such as calcium carbonate has been reported (KR 10-2016-0056420). However, the carbon dioxide mineralization process converts carbon dioxide only to a carbonate form for simple storage, which leads to a limitation in the utilization of the carbon dioxide mineralization process in industrial applications such as cement and papermaking. In addition, there is a problem in that an excessive amount of feed is required for carbon dioxide conversion, resulting in large costs for transporting the feed.

Biological treatment methods and chemical methods for carbon dioxide conversion have been developed, which use microorganisms to fix and convert carbon dioxide, and hydrogen and reducing power are needed to convert carbon dioxide to a useful organic substance. When carbon dioxide is converted by a chemical method, the reforming reaction of methane or ethane or the electrolysis of water is required, and a problem arises in that the generation of carbon dioxide is caused during the reforming reaction of methane or ethane. However, photosynthetic reactions or chemolithotrophic reactions are naturally occurring carbon dioxide fixing reactions that can reduce carbon dioxide without supplying an additional energy source. In addition, since chemolithotrophs grow faster and the carbon dioxide fixing rate thereof is 5 to 10 times higher than photosynthetic organisms, they are more advantageously applied to commercial processes than photosynthetic organisms if an inorganic source is sufficiently supplied thereto.

Accordingly, the present inventors have found that when a carbon dioxide mineralization reaction is used in combination with the metabolism of a sulfur-oxidizing microorganism, a carbonate produced in the carbon dioxide mineralization reaction can be converted to a useful substance without supplying an external additional energy source and mineral resources (metal ions) and the carbon dioxide mineralization reaction can be continuously performed, thereby completing the present invention.

The information disclosed in the Background Art section is only for the enhancement of understanding of the background of the present invention, and therefore may not contain information that forms a prior art that would already be known to a person of ordinary skill in the art.

DISCLOSURE OF INVENTION

Technical Problem

It is an object of the present invention to provide a method of continuously converting carbon dioxide to a useful substance without supplying an external additional energy source (light, electrical energy, etc.) and mineral resources (metal ions).

Technical Solution

To achieve the above object, the present invention provides a process of converting carbon dioxide to a useful substance, comprising: (a) a carbon dioxide mineralization step of reacting carbon dioxide with a metal sulfate, thereby producing a metal-carbonate product and sulfuric acid; (b) a step of culturing a sulfur-oxidizing microorganism in the presence of the produced metal-carbonate product and sulfur, thereby producing a useful substance and a metal sulfate by the sulfur-oxidizing microorganism; and (c) a step of recovering each of the useful substance and metal sulfate produced in step (b), and recycling the recovered metal sulfate to the carbon dioxide mineralization step of step (a).

EXPLANATION ON SYMBOLS

100: a mineralization process
101: an enzyme immobilization unit
102: a carbon dioxide capture unit
103: an electrochemical reaction unit
104: a mineralization unit
105: a separation unit
200: a fermentation process

BEST MODE FOR CARRYING OUT THE INVENTION

Unless defined otherwise, all the technical and scientific terms used herein have the same meaning as those generally understood by one of ordinary skill in the art to which the invention pertains. Generally, the nomenclature used herein and the experiment methods, which will be described below, are those well known and commonly employed in the art.

The present inventors have made extensive efforts to overcome the disadvantages of a conventional carbon dioxide mineralization process that requires a large amount of metal ions and can store carbon dioxide only as a simple carbonate form. As a result, the present inventors have found that when the carbon dioxide mineralization process is used in combination with the metabolism of a sulfur-oxidizing microorganism, a carbonate can be converted to a useful substance without supplying an external additional energy source and mineral resources (metal ions) and the carbon dioxide conversion process can be continuously performed by recycling metal ions.

Therefore, in one aspect, the present invention is directed to a process of converting carbon dioxide to a useful substance, comprising: (a) a carbon dioxide mineralization step of reacting carbon dioxide with a metal sulfate, thereby producing a metal-carbonate product and sulfuric acid; (b) a step of culturing a sulfur-oxidizing microorganism in the presence of the produced metal-carbonate product and sulfur, thereby producing a useful substance and a metal sulfate by the sulfur-oxidizing microorganisms; and (c) a step of recovering each of the useful substance and metal sulfate produced in step (b), and recycling the recovered metal sulfate to the carbon dioxide mineralization step of step (a).

In the present invention, the metal may be an alkali metal. Specifically, the alkali metal may be selected from the group consisting of Ca, Mg, Fe, Si and Al, but is not limited thereto.

In the present invention, the step (a) may comprise steps of: (i) converting carbon dioxide to a carbonate/bicarbonate in a reactor containing a basic solution and a metal sulfate; (ii) reacting the carbonate/bicarbonate with the basic solution, thereby producing a water-soluble carbonate; (iii) reacting the water-soluble carbonate with the metal sulfate, thereby forming a metal-carbonate and a water-soluble sulfate; (iv) separating the water-soluble sulfate into sulfuric acid and a basic solution by electrolysis; and (v) recovering the basic solution produced in step (iv) and recycling the recovered basic solution to step (ii) of producing the water-soluble carbonate.

In the present invention, the step (i) may be facilitated by carbonic anhydrase.

In the step (i) of the present invention, carbon dioxide ($CO_2$) is converted to hydrogen carbonate ($HCO_3^-$), and then sodium carbonate ($Na_2CO_3$) is formed. Hence, when carbon dioxide is dissolved to carbonic acid ($H_2CO_3$) using carbonic anhydrase, a reaction with sodium hydroxide (NaOH) is shortened.

In the present invention, the step (b) may comprise further adding, as an electron receptor, at least one selected from the group consisting of oxygen ($O_2$), nitrate ($NO_3^-$) and nitrite ($NO_2^-$).

In the present invention, the recovery of the metal sulfate in step (c) may be performed by passing the mixture produced in step (b) through a filter to thereby filter the metal sulfate, and then drying the filtered metal sulfate.

In the present invention, the sulfur-oxidizing microorganism may be selected from the group consisting of *Acidianus ambivalans*, *Acidianus brierleyi*, *Aquifex pyrophylus*, *Hydrogenobacter acidophilus*, *Hydrogenobacter thermophiles*, *Thiobacillus denitrificans*, *Thiomicrospira crunogena*, the genus *Sulfurimonas*, the genus *Halothiobacillus*, the genus *Acidithiobacillus*, and *Thermithiobacillus tepidarius*, but is not limited thereto.

In the present invention, the genus *Sulfurimonas* may be selected from the group consisting of *Sulfurimonas autotrophica*, *Sulfurimonas denitrificans*, *Sulfurimonas gotlandica*, and *Sulfurimonas paralvinellae*, the genus *Halothiobacillus* may be selected from the group consisting of *Halothiobacillus halophilus*, *Halothiobacillus hydrothermalis*, *Halothiobacillus kellyi*, and *Halothiobacillus neapolitanus* and the genus *Acidithiobacillus* may be selected from the group consisting of *Acidithiobacillus albertensis*, *Acidithiobacillus caldus*, *Acidithiobacillus cuprithermicus*, *Acidithiobacillus ferridurans*, *Acidithiobacillus ferrivorans*, *Acidithiobacillus ferrooxidans*, and *Acidithiobacillus thiooxidans*, and may preferably be *Acidithiobacillus thiooxidans*, but is not limited thereto.

In the present invention, the useful substance produced by the sulfur-oxidizing microorganism may be selected from the group consisting of PHA (polyhydroxyalkanoate), ethanol, acetic acid, lactic acid, glycerol, 3-hydroxypropionic acid, isobutanol, isobutyric acid, succinic acid, butyric acid, n-butanol, 1,3-propanediol (1,3-PDO), 2,3-butanediol (2,3-BDO), 1,4-butanediol (1,4-BDO), glutamate, isoprene, adipic acid, muconic acid, amino acid, glutathione, polypeptide, phospholipid, polyamine, s-adenosylmethionine, and fatty acid, but is not limited thereto.

In the present invention, a metabolite of *Acidithiobacillus thiooxidans* may be glutamic acid, aspartic acid, glutathione, licanantase, phosphatidylinositol, or spermidine, but is not limited thereto.

In the present invention, the useful substance may be detected by use of a high-performance liquid chromatography (HPLC) method, a gas chromatography (GC) method, or the like.

In the present invention, the step (a) corresponds to a carbon dioxide mineralization reaction and includes a carbonization process and a mineralization process. The carbonization process is a process of converting carbon dioxide to a carbonate/bicarbonate form and may be performed using a method in which carbon dioxide is dissolved in water or a biocatalyst such as carbonic anhydrase is used. Preferably, in the present invention, carbonic anhydrase is used in order to promote the production of the carbonate/bicarbonate.

In addition, the step (a) comprises reacting the carbonate/bicarbonate with the basic solution, thereby producing a water-soluble carbonate. In the present invention, the basic solution comprises sodium hydroxide (NaOH) or potassium hydroxide (KOH), but is not limited thereto. The water-soluble carbonate comprises sodium carbonate ($Na_2CO_3$), sodium hydrogen carbonate ($NaHCO_3$), potassium carbonate ($K_2CO_3$), or potassium hydrogen carbonate ($KHCO_3$), but is not limited thereto.

In addition, the step (a) comprises reacting the water-soluble carbonate with the metal sulfate, thereby forming a metal carbonate (solid carbonate) and a water-soluble sulfate. The metal sulfate may be $CaSO_4$ or $MgSO_4$, and the water-soluble sulfate may be $Na_2SO_4$ or $K_2SO_4$, but is not limited thereto. The solid carbonate may be precipitated and separated from an aqueous solution.

The water-soluble sulfate may be separated into sulfuric acid ($H_2SO_4$) and a basic solution (NaOH, KOH) by electrolysis (electrochemical process). The produced basic solution may be recycled in a step of producing the water-soluble carbonate.

In order for the metal carbonate (solid carbonate) to be produced, a metal element is required, and to complete the reaction and increase the water solubility of carbon dioxide in the carbonization process, alkaline conditions are required. Preferably, the metal element that can be used in the present invention may be a $^{2+}$ metal, such as Ca or Ma, but is not limited thereto. The metal carbonate (solid carbonate) may be $CaCO_3$ or $MgCO_3$, but is not limited thereto.

The above-described production reaction is as shown in Table 1 below.

TABLE 1

$CaO\ (s) + H_2O \rightarrow Ca(OH)_2\ (s)$
$HCO_3^-\ (aq) + Ca(OH)_2\ (aq) \rightarrow CaCO_3\ (s) + 2H_2O$ In the present invention, the carbonic anhydrase may be used as a biocatalyst that reacts nucleophilically with carbon dioxide to form a bicarbonate and then is exchanged with water to promote the production of the bicarbonate. The carbonic anhydrase includes alpha, beta, gamma and delta forms, but is not limited to a particular enzyme derived from plants, animals, Archaea, bacteria, fungi or the like. The reaction equation is as shown in Table 2 below.

TABLE 2 a) E, $ZnH_2O \leftrightarrow$ E, $ZnOH^- + H^+$
b) E, $ZnOH^- + CO_2 \leftrightarrow$ E, $ZnHCO_3^{2-}$
c) E, $ZnHCO_3^{2-} + H_2O \leftrightarrow$ E, $ZnH_2O + HCO_3^{2-}$ In the present invention, the step (b) uses the metabolism of an obligate aerobic chemolithotrophic microorganism, and comprises a process that fixes carbon dioxide using energy generated by oxidation of the electron donor sulfur with the electron acceptor oxygen under growth conditions of the microorganism.

When oxygen is used as an electron acceptor in the metabolism of the chemolithotrophs of the present invention, productivity and capacity are improved compared to when nitrate is used as an electron acceptor in sulfur-limestone autotrophic denitrification (SLAD) which is a metabolism of conventional chemolithotrophs.

In addition, the present invention comprises a process in which the sulfate ion obtained by the oxidation reaction reacts with the metal carbonate, thereby producing a metal sulfate (solid sulfate) and carbon dioxide. The metal carbonate can protect microorganism from the sulfate. The growth condition of the microorganism is characterized by following the optimum growth conditions of a microorganism used under aerobic conditions. Further, the carbon oxide may be converted to a useful substance such as PHA (Polyhydroxyalkanoates), glutamic acid or the like by the microorganism.

In the present invention, the step (c) comprises a process of recovering the metal sulfate (solid sulfate) and recycling the recovered metal sulfate (solid sulfate) in step (a).

In the present invention, the sulfur-oxidizing microorganism is characterized in that they grows using, as a carbon source, carbon dioxide generated by oxidizing sulfur to sulfate, under aerobic conditions, and converts it to organic substances such as PHA (polyhydroxyalkanoate), ethanol, acetic acid, lactic acid, glycerol, 3-hydroxypropionic acid, isobutanol, isobutyric acid, succinic acid, butyric acid, n-butanol, 1,3-propanediol (1,3-PDO), 2,3-butanediol (2,3-BDO), 1,4-butanediol (1,4-BDO), glutamate, isoprene, adipic acid, muconic acid, and fatty acid.

Representative chemolithotrophs and the characteristics thereof are shown in Table 3 below.

TABLE 3

| | *S. Paralyvinellae* $GO25^T$ | *S. sp.* NBC37-1 | *S. Gotlandica* $GD1^T$ | *S. Denitrificans* $DSM1251^T$ | *Sulfurihydrogenibium azorense* Az-$Ful^T$ |
|---|---|---|---|---|---|
| Cell shape | Rod | Rod | Curved Rods to Spiral-like | Rods to Spiral-like | Rod |
| Mobility | + | − | + | − | + |
| Tm (° C.) | 30 | 33 | 15 | 22 | 68 |
| pH | 6.1 | — | 6.0 | 7.0 | 6.0 |
| Electron donor | $H_2, S^0,$ $S_2O_3^{2-}$ | $H_2, S^{2-},$ $S^0,$ $S_2O_3^{2-}$ | $H_2, HS^-,$ $S^0, S_2O_3^{2-},$ Organic substrates | $HS^-, S_2O_3^{2-},$ Organicsubstrates | $H_2, S^0, S_2O_3^{2-},$ $Fe^{2+}, SO_3^{2-},$ $AsO_3^{3-}$ |
| Electron acceptor | $O_2, NO_3^-$ | $O_2, NO_3^-$ | $NO_3^-, NO_2^-$ | $O_2, NO_3^-, NO_2^-$ | $O_2, S^0, Fe^{3+}, SO_3^{2-},$ $SeO_4^{2-},$ $AsO_4^{2-}$ |

In another aspect, the present invention is directed to a process of converting carbon dioxide to a useful substance, comprising: (i) a step of reacting carbon dioxide with a basic solution and carbonic anhydrase, thereby converting the carbon dioxide to a carbonate/bicarbonate; (ii) a carbon dioxide capture step of reacting the carbonate/bicarbonate with the basic solution, thereby producing a water-soluble carbonate; (iii) a mineralization step of adding a metal sulfate to the produced water-soluble carbonate, thereby forming a metal carbonate and a water-soluble sulfate; (iv) a step of separating the metal carbonate from the water-soluble sulfate formed in the step (iii); (v) a step of separating the separated water-soluble sulfate into sulfuric acid and a basic solution by electrolysis, and recovering and recycling the basic solution to the carbon dioxide capture step of the step (ii); (vi) a step of adding sulfur, an electron acceptor and a sulfur-oxidizing microorganism to the metal carbonate separated in the step (iv), followed by culturing, thereby producing a mixture of a useful substance and a metal sulfate; and (vii) a step of passing the mixture produced in the step (vi) through a filter, thereby recovering each of the useful substance and the metal sulfate, and then drying and recycling the recovered metal sulfate to the carbon dioxide mineralization step of the step (iii).

EXAMPLES

Hereinafter, the present invention will be described in further detail with reference to examples. It will be obvious to a person having ordinary skill in the art that these examples are for illustrative purposes only and are not to be construed to limit the scope of the present invention.

Example 1: Carbon Dioxide Mineralization Reaction

Figure 1:
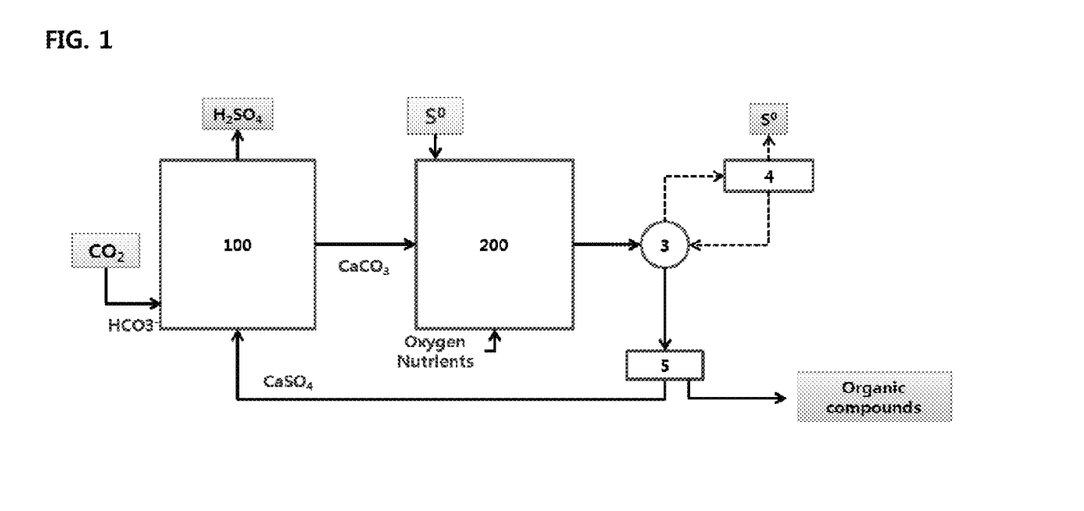
FIG. 1 shows a process in which a metal sulfate ($MeSO_4$) is converted to sulfuric acid and a metal carbonate ($MeCO_3$) by a carbon dioxide mineralization reaction and a sulfur-oxidizing microorganism grows using the metal carbonate ($MeCO_3$) and sulfur and produce organic compounds (system 100: a process in which the metal sulfate ($MeSO_4$) is converted to the metal carbonate ($MeCO_3$) by the carbon dioxide mineralization reaction and sulfuric acid is produced; and system 200: a fermentation process in which a microorganism grows autotrophically using the metal carbonate ($MeCO_3$) and sulfur).

FIG. 1 shows a process in which a metal sulfate ($MeSO_4$) is converted to a metal carbonate ($MeCO_3$) by a carbon dioxide mineralization reaction and sulfur-oxidizing microorganisms grow using the metal carbonate ($MeCO_3$) and sulfur and produce organic compounds.

Figure 2:
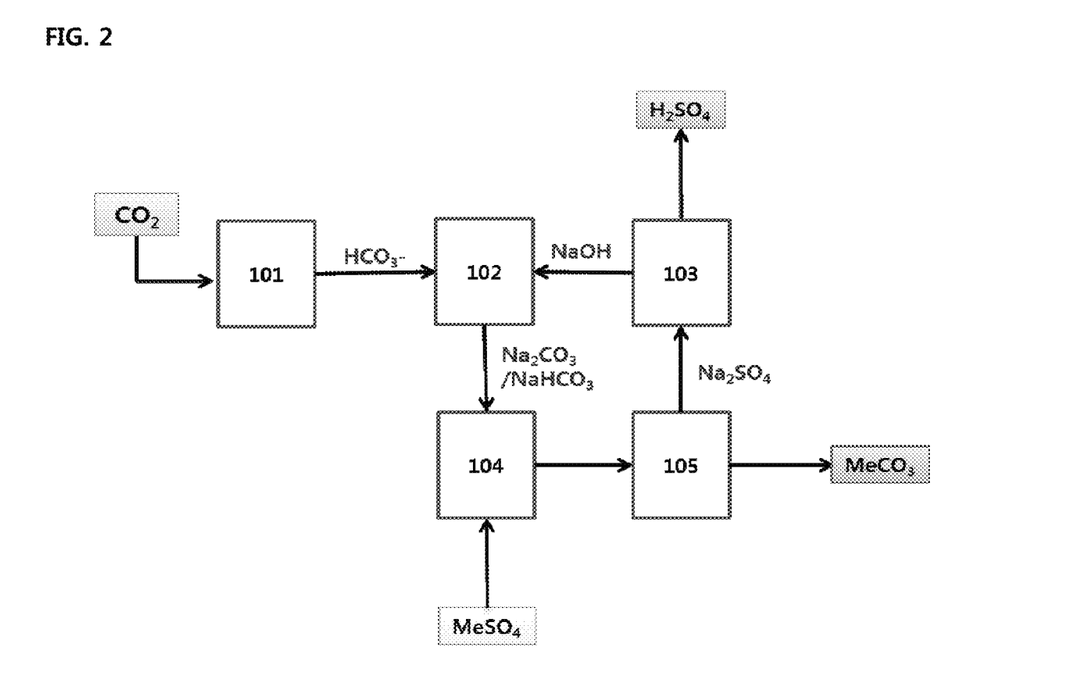
FIG. 2 specifically shows the process of the system 100 shown in FIG. 1 (unit 101: an enzyme immobilization unit that effectively converts carbon dioxide to a bicarbonate by using carbonic anhydrase; unit 102: a carbon dioxide capture unit that produces a mixture of water-soluble carbonates by reacting an alkali solution with bicarbonate; unit 103: an electrochemical reaction unit that separates a water-soluble sulfate into sulfuric acid ($H_2SO_4$) and a basic solution, which are an acid and a base, respectively; unit 104: a mineralization unit that produces a metal carbonate and a water-soluble sulfate by reacting a water-soluble carbonate with a metal sulfate; and unit 105: a separation unit that separates the produced metal carbonate and supplies the water-soluble sulfate (electrolyte) to the unit 103).
Figure 3:
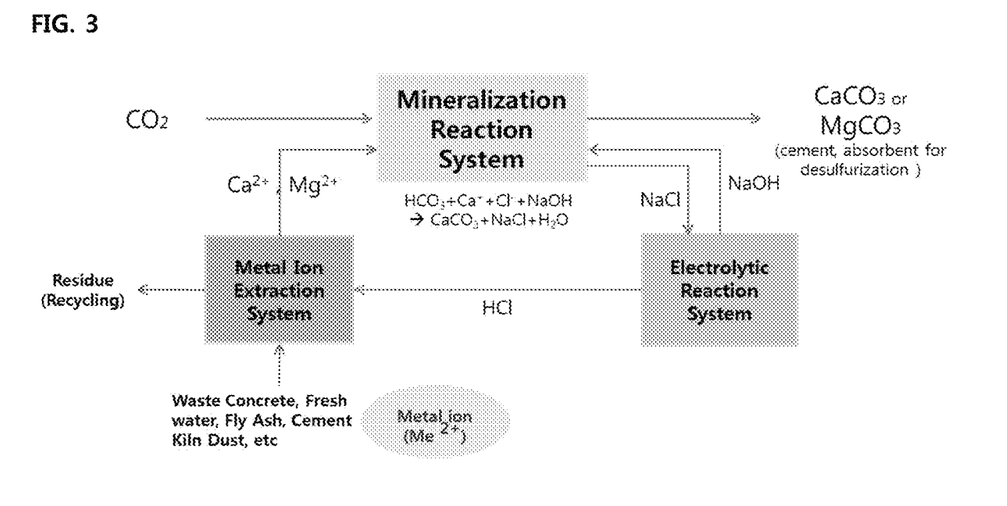
FIG. 3 schematically shows a carbon dioxide mineralization reaction.
Figure 4:
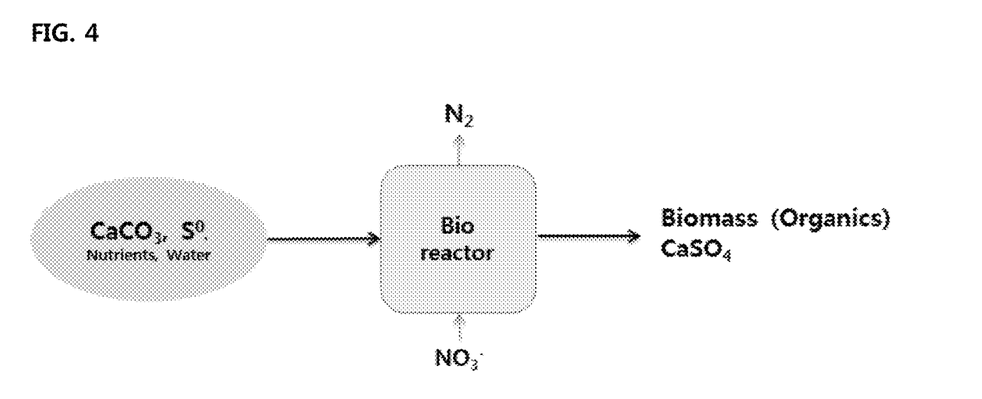
FIG. 4 schematically shows a sulfur denitrification process.

As shown in FIG. 2, carbon dioxide was converted to a bicarbonate by carbonic anhydrase in an enzyme immobilization unit 101 of the mineralization process system. The reaction equation is as follows:

$$E,ZnH_2O \leftrightarrow E,ZnOH^- + H^+$$

$$E,ZnOH^- + CO_2 \leftrightarrow E,ZnHCO_3^{2-}$$

$$E,ZnHCO_3^{2-} + H_2O \leftrightarrow E,ZnH_2O + HCO_3^{2-}.$$

To produce a mixture of water-soluble carbonates, the bicarbonate was reacted with a NaOH basic solution in a carbon dioxide capture unit 102, thereby obtaining water-soluble carbonates ($Na_2CO_3$ and $NaHCO_3$). In a mineralization unit 104, the water-soluble carbonates were reacted with a feed (which is a solid sulfate ($MeSO_4$) of $CaSO_4$), thereby producing a solid carbonate ($MeCO_3$) of $CaCO_3$ and a water-soluble sulfate of $Na_2SO_4$. The metal carbonate was separated, and the solid carbonate was separated in a separation unit 105. The reaction equation is as follows:

$$CaSO_4 + CO_2 + H_2O \rightarrow H_2SO_4 + CaCO_3.$$

The water-soluble sulfate remaining after separation in the separation unit 105 was separated into sulfuric acid ($H_2SO_4$) and a NaOH basic solution by an electrochemical process in an electrochemical reaction unit 103. The basic solution can react again with the bicarbonate in the carbon dioxide capture unit 102.

In a fermentation process unit 200, sulfur (electron donor) as an energy source was converted to sulfate ions ($SO_4^{2-}$) using oxygen (electron acceptor) under optimal conditions for growth of *Acidithiobacillus thiooxidans*. The sulfate ions reacted with the solid carbonate ($MeCO_3$) of $CaCO_3$, thereby producing a solid sulfate of $CaSO_4$ and carbon dioxide. In addition, biomass was produced using the carbon dioxide as a carbon source.

The produced solid sulfate of $CaSO_4$ was recovered and recycled to the mineralization unit 104 in which the carbon dioxide mineralization reaction was performed.

To recover the produced solid sulfate, $CaSO_4$ was filtered by passage through a 20 μm filter, and then dried in an oven overnight at 50° C.

In addition, to mineralize carbon dioxide, a carbon dioxide capture process was performed in which carbon dioxide was reacted with sodium hydroxide (NaOH), thereby producing sodium carbonate ($Na_2CO_3$). The reaction equation is as follows:

$$2NaOH + CO_2 \rightarrow Na_2CO_3 + H_2O.$$

The sodium carbonate was mineralized with calcium sulfate ($CaSO_4$), thereby producing calcium carbonate ($CaCO_3$) and sodium sulfate. The reaction equation is as follows:

$$Na_2CO_3 + CaSO_4 \rightarrow CaCO_3 + Na_2SO_4.$$

After the separation process, the produced calcium carbonate was subjected to a fermentation process with sulfur-containing medium, oxygen and microorganisms in an incubator.

The produced biomass and calcium sulfate were separated from each other in a separator. The biomass was recovered, and the calcium sulfate was recovered and recycled to the mineralization process.

In addition, the sodium sulfate produced by the mineralization reaction was separated into sulfuric acid and sodium hydroxide by electrolysis. Then, the separated sodium hydroxide was recovered and recycled to the carbon dioxide capture process, and the sulfuric acid was discharged. The reaction equation of the electrolysis process is as follows:

$$Na_2SO_4 + 2H_2O \rightarrow H_2SO_4 + 2NaOH.$$

Example 2: Fermentation Process

Figure 5:
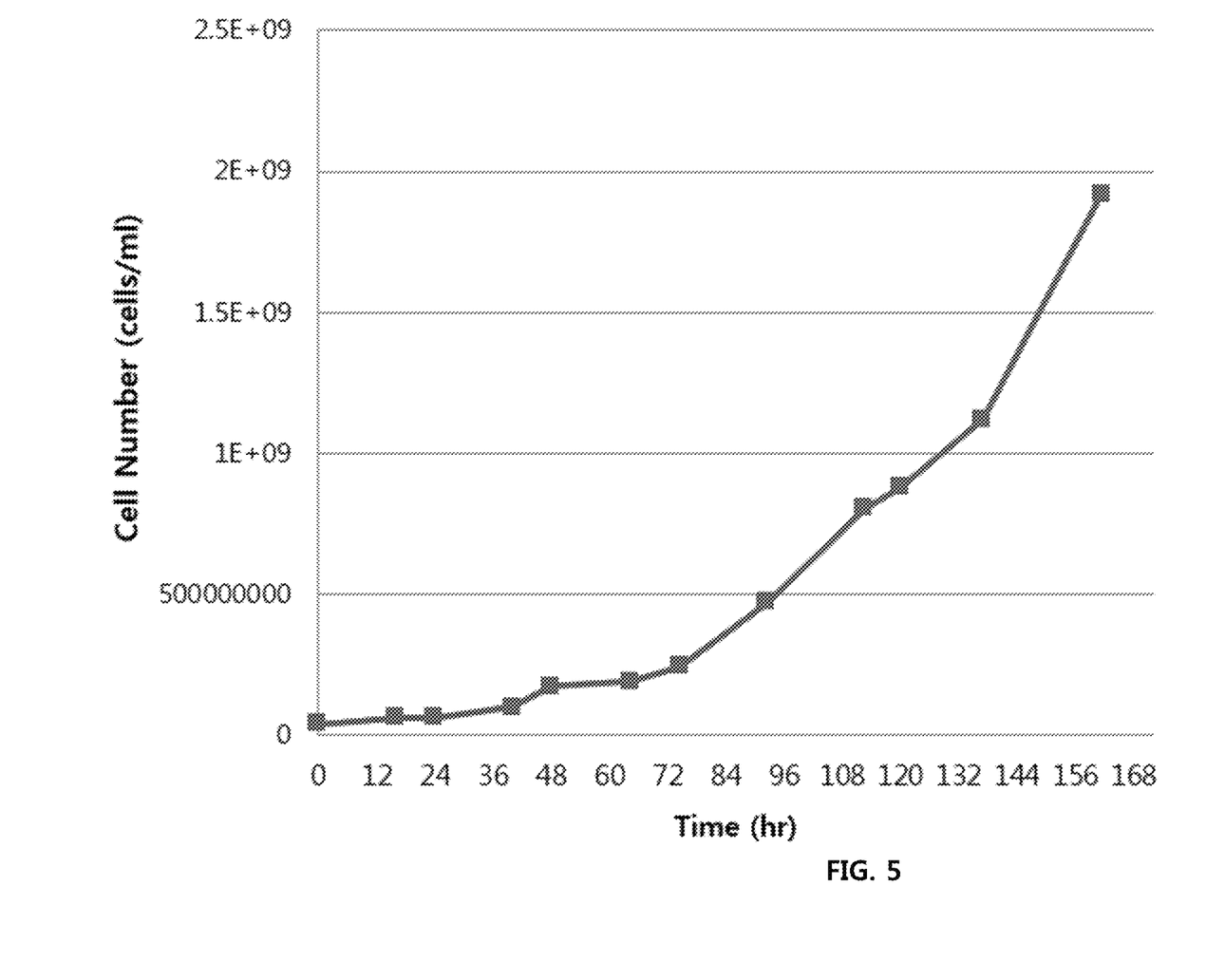
FIG. 5 shows the results of culturing microorganisms using a combination of a carbon dioxide mineralization process and a fermentation process.

In a fermentation process, a useful substance was obtained by microbial fermentation using the calcium carbonate obtained by the mineralization process (FIG. 5).

To confirm a useful substance would be obtained by the fermentation process, 200 ml of medium was placed in a 1000 ml flask, and inoculated with 0.25% *Acidithiobacillus thiooxidans* which was then precultured under the conditions of 30° C. and 150 rpm. Next, 1 L of medium (Table 4) was placed in a 3.5 L fermenter, and then inoculated with 2.5% of the preculture. At this time, the pH decreased from 4.6 to 2.0, and hence culturing was performed under the conditions of 1 vvm air and 350 rpm while the pH was maintained at 3.0 using 200 g/L of $CaCO_3$ solution. As a result, it could be seen that the cell growth increased depending on culture time (Table 5).

The composition of the medium is shown in Table 4 below.

TABLE 4

| Composition | Content |
| --- | --- |
| $(NH_4)_2SO_4$ | 0.2 g/L |
| $MgSO_4 \cdot 7H_2O$ | 0.5 g/L |
| $CaCl_2 \cdot 2H_2O$ | 250 mg/L |
| $KH_2PO_4$ | 3 g/L |
| $FeSO_4 \cdot 7H_2O$ | 10 mg/L |
| sulphur powder | 10 g/L |

The number of cells depending on culture time is shown in Table 5 below.

TABLE 5

| Time (hr) | Cell No. (cells/ml) |
| --- | --- |
| 0 | 3.9E+07 |
| 16 | 6.1E+07 |
| 24 | 6.2E+07 |
| 48 | 1.7E+08 |
| 64.5 | 1.9E+08 |
| 74.5 | 2.4E+08 |
| 92.5 | 4.7E+08 |
| 112.5 | 8E+08 |
| 120 | 8.8E+08 |
| 137 | 1.1E+09 |
| 161.5 | 1.9E+09 |

Example 3: Analysis of Useful Substances

To detect S-adenosylmethionine among the useful substances produced in Example 2, an HPLC-UV method and a GC-FID method were used.

In the HPLC-UV method, as a column, a waters symmetry C18 column (4.6×250 mm) was used, and as a detector, a UV 254 nm detector was used. The flow rate was 1.0 ml/min. Water was used as mobile phase A, and acetonitrile was used as a mobile phase B. Elution was performed for 2 minutes at 85% water and 15% acetonitrile, 10 minutes at 100% acetonitrile, minutes at 100% acetonitrile, 16 minutes at 15% acetonitrile, and 25 minutes at 15% acetonitrile.

Figure 6:
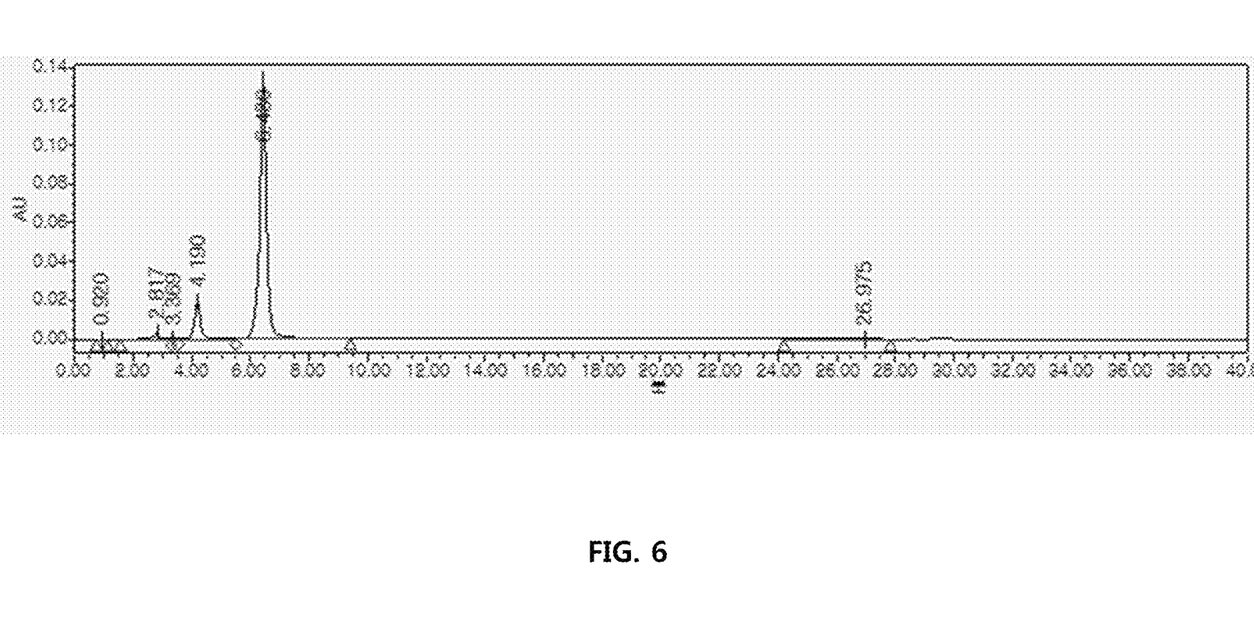
FIG. 6 shows the results of analyzing S-adenosylmethionine, produced according to the present invention, by HPLC chromatography.

As a result, it was confirmed that S-adenosylmethionine was detected at a retention time of 6.430 minutes (FIG. 6).

To detect spermidine among the useful substances produced in Example 2, 200 µl of the sample obtained in Example 2 was mixed with 200 µl of a solution obtained by mixing chloroform with isooctane at a volume ratio of 1:4, and 50 µl of $K_2CO_3$—$KHCO_3$ buffer (pH 12.2) was added to the resulting mixture. Next, 1 µl of propyl chloroformate was added thereto, followed by vortexing. Then, the mixture was centrifuged at 13,000 rpm for 5 minutes. 100 µl of the resulting upper organic layer was analyzed by GC.

In the GC-FID method, as a column, a HP-5 column (30 m×320 µm×0.25 µm) was used, and as a detector, an FID (flame ionization detector) was used. The detection temperature was 250° C. Helium was used as a carrier gas, and the oven temperature was initially maintained at 50° C. for 1 minute, and then was increased to 280° C. at a rate of 20° C./minute, and then maintained at that temperature for 5 minutes.

Figure 7:
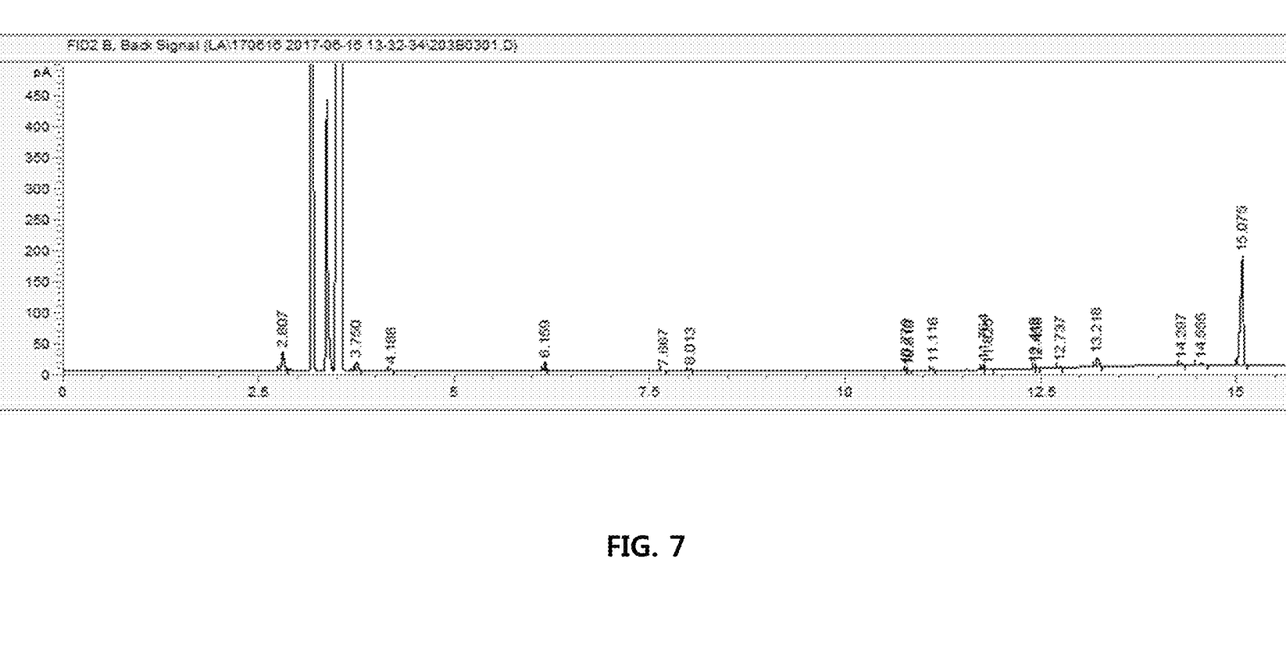
FIG. 7 shows the results of analyzing spermidine, produced according to the present invention, by GC-FID.

As a result, it was confirmed that spermidine was detected at a retention time of 15.075 minutes (FIG. 7).

The process of converting carbon dioxide is performed by using a combination of a carbon dioxide mineralization and the metabolism of a sulfur-oxidizing microorganism. According to the process, a carbonate produced in the carbon dioxide mineralization reaction can be converted to a useful substance without supplying an external additional energy source (light, electrical energy, etc.) and mineral resources (metal ions). In addition, the process can be continuously performed by recycling metal ions necessary for the carbon dioxide mineralization reaction.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A process of converting carbon dioxide to a useful substance which is s-adenosylmethionine or spermidine, comprising:
    (a) (i) converting carbon dioxide to a carbonate/bicarbonate by carbonic anhydrase in a reactor;
       (ii) reacting the carbonate/bicarbonate with a basic solution, thereby producing a water-soluble carbonate;
       (iii) reacting the water-soluble carbonate with a solid metal sulfate, thereby forming a metal-carbonate and a water-soluble sulfate;
       (iv) separating the water-soluble sulfate into sulfuric acid and a basic solution by electrolysis; and
       (v) recovering the basic solution produced in step (iv) and recycling the recovered basic solution to step (ii) of producing the water-soluble carbonate;
    (b) culturing *Acidithiobacillus thiooxidans* in the presence of a produced metal-carbonate product, sulfur as an electron donor, and oxygen ($O_2$) as an electron acceptor, thereby producing the useful substance and a solid metal sulfate by the *Acidithiobacillus thiooxidans*; and
    (c) recovering each of the useful substance and the solid metal sulfate produced in step (b), and recycling the recovered solid metal sulfate to the step iii) of step (a).

2. The process of claim 1, wherein the metal is an alkali metal.

3. The process of claim 2, wherein the alkali metal is selected from the group consisting of Ca, Mg, Fe, Si and Al.

4. The process of claim 1, wherein the recovery of the solid metal sulfate in step (c) is performed by passing a mixture produced in step (b) through a filter to thereby filter the solid metal sulfate, and then drying the filtered solid metal sulfate.

5. A process of converting carbon dioxide to a useful substance which is s-adenosylmethionine or spermidine, comprising:
    (i) converting carbon dioxide to a carbonate/bicarbonate by carbonic anhydrase in a reactor;
    (ii) reacting the carbonate/bicarbonate with a basic solution, thereby producing a water-soluble carbonate;
    (iii) reacting the water-soluble carbonate with a solid metal sulfate, thereby forming a metal carbonate and a water-soluble sulfate;
    (iv) separating the metal carbonate from the water-soluble sulfate formed in step (iii);
    (v) separating the separated water-soluble sulfate into sulfuric acid and a basic solution by electrolysis, and recovering and recycling the basic solution to step (ii);
    (vi) adding sulfur as an electron donor, oxygen ($O_2$) as an electron acceptor, and *Acidithiobacillus thiooxidans* to the metal carbonate separated in step (iv), followed by culturing *Acidithiobacillus thiooxidans*, thereby producing a mixture of the useful substance and a solid metal sulfate; and (vii) passing the mixture produced in step (vi) through a filter, thereby recovering each of the useful substance and the solid metal sulfate, and then drying and recycling the recovered solid metal sulfate to step (iii).

6. The method of claim 2, wherein the recovery of the solid metal sulfate in step (c) is performed by passing a mixture produced in step (b) through a filter to thereby filter the solid metal sulfate, and then drying the filtered solid metal sulfate.

7. The process of claim 1, wherein the solid metal sulfate is metal $SO_4$.

* * * * *